United States Patent [19]

Barnes

[11] Patent Number: 5,962,742

[45] Date of Patent: Oct. 5, 1999

[54] PROCESS FOR THE PREPARATION OF 5-BROMO-2 FLUOROBENZENEBORONIC ACID

[75] Inventor: Keith D. Barnes, Newtown, Pa.

[73] Assignee: American Cyanamid Company, Madison, N.J.

[21] Appl. No.: 08/871,025

[22] Filed: Jun. 6, 1997

Related U.S. Application Data

[60] Provisional application No. 60/019,906, Jun. 14, 1996.
[51] Int. Cl.$^6$ ...................................................... C07F 5/02
[52] U.S. Cl. ................................................ 568/6; 568/1
[58] Field of Search .............................................. 568/1, 6

[56] References Cited

U.S. PATENT DOCUMENTS

| | | |
|---|---|---|
| 2,898,365 | 8/1959 | Washburn . |
| 3,090,801 | 5/1963 | Washburn . |
| 5,068,403 | 11/1991 | Elliott et al. ................................. 562/7 |
| 5,283,371 | 2/1994 | Elliott et al. ............................. 568/639 |

FOREIGN PATENT DOCUMENTS

| | | | |
|---|---|---|---|
| 0 238 272 | 9/1987 | European Pat. Off. .......... | C07F 5/02 |
| 0 440 082 | 8/1991 | European Pat. Off. .......... | C07F 5/02 |
| 2187731 | 9/1987 | United Kingdom .............. | C07F 5/02 |
| 2226315 | 6/1990 | United Kingdom .............. | C07F 3/02 |
| 2288803 | 1/1995 | United Kingdom .......... | C07C 43/225 |
| WO 94/06741 | 3/1994 | WIPO ............................ | C07C 43/29 |

OTHER PUBLICATIONS

A.W. Farnham, et al., *Pesticide Science*, 28, pp. 25–34 (1990).

A.J. Bridges, et al., *Tetrahedron Letters*, 33, pp. 7495–7498 (1992).

J Org Chem, "Different Product from Lithiation of Ploy-fluorobromobenzenes in Ether and THF", Bridges, 55, pp. 773–775, Jan. 1990.

CA 124:232038, abst of GB 2288803, 1995.

D. Ladd, et al. "Improved Synthesis of Fluoroveratroles and Fluorophenethylamines via Organolithium Reagents", J. Org. Chem. 46, 203–206 (1981).

*Primary Examiner*—Gary Geist
*Assistant Examiner*—Jean F. Vollano
*Attorney, Agent, or Firm*—Timothy J. Babcock

[57] ABSTRACT

A process is disclosed for the preparation of 5-bromo-2-fluorobenzeneboronic acid, which is useful as an intermediate in the preparation of a non-ester pyrethroid compound. The compound can be, for example, a fluoroolefin, which is useful as a pesticide.

10 Claims, No Drawings

PROCESS FOR THE PREPARATION OF 5-BROMO-2 FLUOROBENZENEBORONIC ACID

This application claims benefit of provisional application Ser. No. 60/019,906 filed Jun. 14, 1996.

BACKGROUND AND SUMMARY OF THE INVENTION

5-Bromo-2-fluorobenzeneboronic acid is an important intermediate in the synthesis of a number of non-ester pyrethroid compounds. 5-Bromo-2-fluorobenzeneboronic acid and processes for its preparation are described in U.S. Pat. No. 5,068,403 and Pesticide Science, 28, pp. 25–34 (1990), which are incorporated herein by reference. Those references disclose that 5-bromo-2-fluorobenzeneboronic acid is prepared from 2,4-dibromofluorobenzene. However, 2,4-dibromofluorobenzene is not entirely satisfactory for use in the commercial manufacture of 5-bromo-2-fluorobenzeneboronic acid.

2,4-Dibromofluorobenzene is commercially available as a mixture containing seventy percent 2,4-dibromofluorobenzene and thirty percent 3,4-dibromofluorobenzene. When that mixture is used to prepare 5-bromo-2-fluorobenzeneboronic acid, at most, only a 70% yield is obtainable based on the total amount used. In addition, to obtain high purity 5-bromo-2-fluorobenzeneboronic acid, a time-consuming purification step is required to remove impurities such as 3,4-dibromofluorobenzene. A process that avoids the use of 2,4-dibromofluorobenzene would provide a great improvement over the art processes.

It is therefore an object of the present invention to provide a process for the preparation of 5-bromo-2-fluorobenzeneboronic acid which avoids the use of 2,4-dibromofluorobenzene.

The present invention provides a process for the preparation of 5-bromo-2-fluorobenzeneboronic acid which comprises lithiating 1-bromo-4-fluorobenzene with a lithium base in the presence of a solvent to form (5-bromo-2-fluorophenyl)lithium, reacting (5-bromo-2-fluorophenyl)lithium with a tri($C_1$–$C_6$alkyl) borate to form a di($C_1$–$C_6$alkyl) 5-bromo-2-fluorobenzeneboronate, and hydrolyzing the di($C_1$–$C_6$alkyl) 5-bromo-2-fluorobenzeneboronate. It has been found that the process of this invention is more effective and efficient than the prior art processes, and avoids the use of 2,4-dibromofluorobenzene which is commercially availably only as an impure mixture.

The present invention also provides a process for the preparation of a fluoroolefin compound of formula I

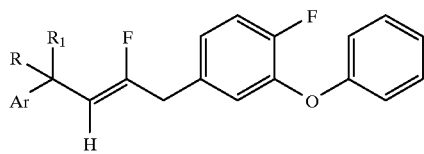

(I)

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is hydrogen and $R_1$ is cyclopropyl, or R and $R_1$ are each independently $C_1$–$C_4$alkyl, or R and $R_1$ are taken together with the carbon atom to which they are attached to form a cyclopropyl group.

The configuration of the hydrogen atom and the fluorine atom about the double bond is mutually trans. The process comprises lithiating 1-bromo-4-fluorobenzene with a lithium base in the presence of a solvent to form (5-bromo-2-fluorophenyl)lithium, reacting (5-bromo-2-fluorophenyl)lithium with a tri($C_1$–$C_6$alkyl) borate to form a di($C_1$–$C_6$alkyl) 5-bromo-2-fluorobenzeneboronate, hydrolyzing the di($C_1$–$C_6$alkyl) 5-bromo-2-fluorobenzeneboronate to form 5-bromo-2-fluorobenzeneboronic acid, oxidizing 5-bromo-2-fluorobenzeneboronic acid to form 5-bromo-2-fluorophenol, reacting 5-bromo-2-fluorophenol with bromobenzene and a base such as sodium hydride to form 5-bromo-2-fluorophenyl ether, reacting 5-bromo-2-fluorophenyl ether with magnesium, and reacting the resulting compound in the presence of a transition metal catalyst such as a cuprous halide, cuprous cyanide or $Li_2CuCl_4$ to form the desired fluoroolefin of formula I. The fluoroolefin compound is useful in a pesticide composition.

Compounds of Formula I may have a trans or cis configuration of the hydrogen and fluorine atom about the double bond. Compounds having a trans configuration are preferred, and are prepared by using the reactant III (as described below) having a trans configuration. To prepare compounds of Formula I with a cis configuration, a reactant III having a cis configuration is used. To prepare compounds of Formula I having a mixture of trans and cis configurations, a reactant III having a mixture of trans and cis configurations is used.

The invention is described in the following specific embodiments:

1. A process for preparing 5-bromo-2-fluorobenzeneboronic acid, the process comprises lithiating 1-bromo-4-fluorobenzene to form (5-bromo-2-fluorophenyl)lithium; reacting (5-bromo-2-fluorophenyl) lithium with a tri($C_1$–$C_6$alkyl) borate to form a di($C_1$–$C_6$ alkyl) 5-bromo-2-fluorobenzeneboronate; and hydrolyzing the di($C_1$–$C_6$ alkyl) 5-bromo-2-fluorobenzeneboronate.

2. The process of embodiment 1 wherein the lithiating step is at a temperature of less than about 0° C.

3. The process of embodiment 2 wherein the temperature is less than about –40° C.

4. The process of embodiment 1 wherein the 1-bromo-4-fluorobenzene in the lithiating step is reacted with a lithium base.

5. The process of embodiment 4 wherein the lithium base is a lithium dialkylamide or a lithium cyclic amide.

6. The process of embodiment 4 wherein the 1-bromo-4-fluorobenzene in the lithiating step is reacted with the base in the presence of a solvent.

7. The process of embodiment 6 wherein the solvent is an ether.

8. The process of embodiment 1 wherein the tri($C_1$–$C_6$alkyl) borate is trimethyl borate.

9. The process of embodiment 1 wherein the di($C_1$–$C_6$alkyl) 5-bromo-2-fluorobenzeneboronate is hydrolyzed with an organic or mineral acid.

10. The process of embodiment 9 wherein the organic or mineral acid is an aqueous acid.

11. A process for the preparation 5-bromo-2-fluorobenzeneboronic acid which comprises lithiating 1-bromo-4-fluorobenzene with a lithium base in the presence of a solvent to form (5-bromo-2-fluorophenyl)lithium, reacting (5-bromo-2-fluorophenyl)lithium with tri (C$_1$–C$_6$alkyl) borate to form a di(C$_1$–C$_6$alkyl) 5-bromo-2-fluorobenzeneboronate, and hydrolyzing the di(C$_1$–C$_6$alkyl) 5-bromo-2-fluorobenzeneboronate.

12. The process according to embodiment 11 wherein 1-bromo-4-fluorobenzene is lithiated with the lithium base at a temperature below about 0° C.

13. The process according to embodiment 12 wherein the temperature is below about −40° C.

14. The process according to embodiment 11 wherein the lithium base is a lithium dialkylamide or a lithium cyclic amide.

15. The process according to embodiment 14 wherein the lithium base is lithium diisopropyl amide.

16. The process according to embodiment 11 wherein the solvent is an ether.

17. The process according to embodiment 16 wherein the ether is tetrahydrofuran.

18. The process according to embodiment 11 wherein the tri(C$_1$–C$_6$alkyl) borate is trimethyl borate.

19. The process according to embodiment 11 wherein the di (C$_1$–C$_6$alkyl) 5-bromo-2-fluorobenzeneboronate is hydrolyzed with an aqueous organic acid or an aqueous mineral acid.

20. A process for the preparation 5-bromo-2-fluorobenzeneboronic acid which comprises lithiating 1-bromo-4-fluorobenzene with a lithium base selected from the group consisting of a lithium dialkylamide and a lithium cyclic amide in the presence of an ether to form (5-bromo-2-fluorophenyl) lithium with a tri(C$_1$–C$_6$alkyl) borate to form a di(C$_1$–C$_6$alkyl) 5-bromo-2-fluorobenzeneboronate, and hydrolyzing the di(C$_1$–C$_6$alkyl) 5-bromo-2-fluorobenzeneboronate with an aqueous organic or mineral acid.

21. A process for preparing a fluoroolefin compound having the formla

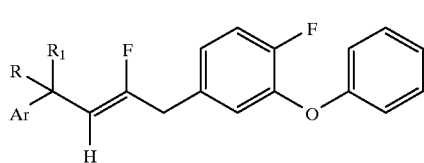
(I)

wherein Ar is phenyl optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups, or 1- or 2-naphthyl optionally substituted with any combination of from one to three halogen, C$_1$–C$_4$alkyl, C$_1$–C$_4$haloalkyl, C$_1$–C$_4$alkoxy or C$_1$–C$_4$haloalkoxy groups; R is hydrogen and R$_1$ is cyclopropyl, or R and R$_1$ are each independently C$_1$–C$_4$alkyl, or R and R$_1$ are taken together with the carbon atom to which they are attached to form a cyclopropyl group; and the configuration of the hydrogen atom and the fluorine atom about the double bond is mutually trans. The process comprises lithiating 1-bromo-4-fluorobenzene with a lithium base in the presence of a solvent to form (5-bromo-2-fluorophenyl)lithium, first reacting (5-bromo-2-fluorophenyl)lithium with a tri (C$_1$–C$_6$alkyl) borate to form a di(C$_1$–C$_6$alkyl) 5-bromo-2-fluorobenzeneboronate, hydrolyzing the di(C$_1$–C$_6$alkyl) 5-bromo-2-fluorobenzeneboronate to form 5-bromo-2-fluorobenzeneboronic acid, oxidizing 5-bromo-2-fluorobenzeneboronic acid to form 5-bromo-2-fluorophenol, second reacting 5-bromo-2-fluorophenol with bromobenzene and a base to form 5-bromo-2-fluorophenyl ether, third reacting 5-bromo-2-fluorophenyl phenyl ether with magnesium to form the corresponding magnesium bromide, and fourth reacting the magnesium bromide with a compound having the formula

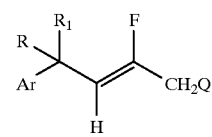

wherein Ar, R and R$_1$ are as described above and Q is OC(O)CH$_3$ or Br in the presence of a transition metal catalyst.

22. The process of embodiment 21 wherein the base in the second reacting step is sodium hydride.

DETAILED DESCRIPTION OF THE INVENTION

The process preferably comprises lithiating 1-bromo-4-fluorobenzene with at least about one molar equivalent of a lithium base in the presence of a solvent preferably at a temperature below about 0° C., more preferably below about −40° C., to form (5-bromo-2-fluorophenyl)lithium, reacting (5-bromo-2-fluorophenyl)lithium with at least about one molar equivalent of a tri(C$_1$–C$_6$alkyl) borate to form a di(C$_1$–C$_6$alkyl) 5-bromo-2-fluorobenzeneboronate, and hydrolyzing the di(C$_1$–C$_6$alkyl) 5-bromo-2-fluorobenzene boronate with at least about two molar equivalents of an aqueous acid to form the desired 5-bromo-2-fluorobenzeneboronic acid. The reaction scheme is shown in Flow Diagram I.

Flow Diagram I

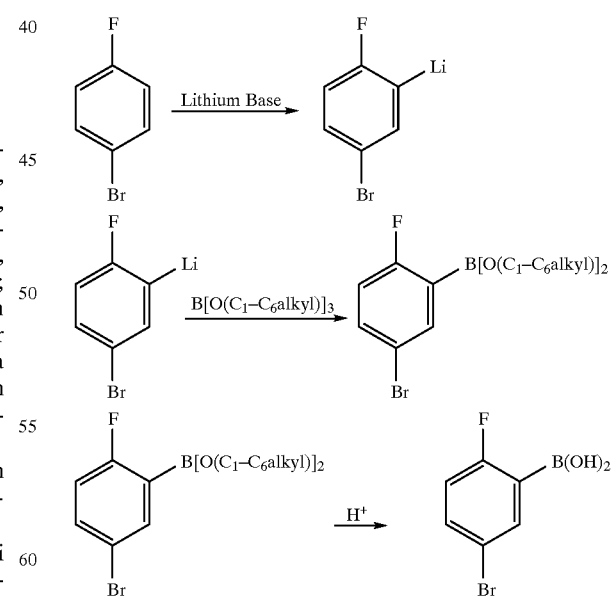

Advantageously, the process of this invention overcomes the problems associated with the use of impure 2,4-dibromofluorobenzene by using 1-bromo-4-fluorobenzene. By avoiding the use of impure 2,4-dibromofluorobenzene, the process of this invention provides 5-bromo-2-fluorobenzeneboronic acid in higher yield and higher purity than the less effective and less efficient art processes.

Lithium bases suitable for use in the process of this invention include lithium secondary amide bases such as lithium dialkylamides, lithium cyclic amides, lithium arylalkylamides and lithium bis(alkylsilyl)amides and alkyl lithiums such as n-butyl lithium, s-butyl lithium, and tert-butyl lithium. Preferred lithium bases include lithium dialkylamides such as lithium diisopropylamide and lithium isopropylcyclohexylamide, lithium cyclic amides such as lithium 2,2,6,6-tetramethylpiperidine, lithium arylalkylamides such as lithium phenylmethylamide, and bis (alkylsilyl)amides such as lithium bis(trimethylsilyl)amide, with lithium diisopropylamide and lithium 2,2,6,6-tetramethylpiperidine being more preferred.

Solvents suitable for use in the process of the present invention include organic solvents which do not react undesirably with any of the compounds present in the reaction mixture. Preferred organic solvents include ethers such as tetrahydrofuran, diethyl ether, 1,2-di-methoxyethane, and mixtures thereof, with tetrahydrofuran being more preferred.

Preferred tri($C_1$–$C_6$alkyl) borates include trimethyl borate, triethyl borate, tri-n-butyl borate and triisopropyl borate with trimethyl borate being more preferred.

The di ($C_1$–$C_6$alkyl) 5-bromo-2-fluorobenzeneboronate compound is preferably hydrolyzed with an aqueous organic acid such as acetic acid, propionic acid and butyric acid or an aqueous mineral acid such as hydrochloric acid and sulfuric acid.

In order to facilitate a further understanding of the invention, the following example is presented to illustrate more specific details thereof. The invention is not to be limited thereby except as defined in the claims.

EXAMPLE 1

Preparation of 5-Bromo-2-fluorobenzeneboronic acid

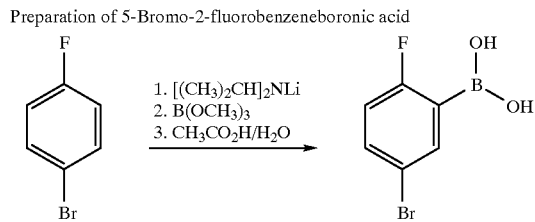

A solution of lithium diisopropylamide (165 mL of a 2.0M solution in tetrahydrofuran, 0.33 mol) in tetrahydrofuran (600 mL) at −70° C. is treated with 1-bromo-4-fluorobenzene (33.0 mL, 0.30 mol), stirred at −70° C. for 90 minutes and added to a solution of trimethyl borate (41.0 mL, 0.36 mol) in diethyl ether (300 mL) at −70° C. The resulting solution is stirred at −70° C. for 15 minutes, warmed to 15° C. over 90 minutes, treated with acetic acid (51.5 mL, 0.9 mol) and water (375 mL), and stirred at room temperature for 30 minutes. The organic layer is separated and the aqueous layer is extracted with ether. The organic extracts are combined with the organic layer and the resulting solution is washed sequentially with 10% hydrochloric acid and brine, dried over anhydrous magnesium sulfate and concentrated in vacuo to give the title product as an off-white solid (65 g, 99% yield).

Advantageously, the present invention also provides a process for the preparation of a fluoroolefin compound of formula I

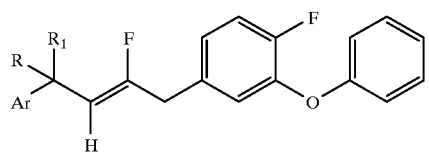

wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups; R is hydrogen and $R_1$ is cyclopropyl, or R and $R_1$ are each independently $C_1$–$C_4$alkyl, or R and $R_1$ are taken together with the carbon atom to which they are attached to form a cyclopropyl group; and the configuration of the hydrogen atom and the fluorine atom about the double bond is mutually trans.

The process comprises lithiating 1-bromo-4-fluorobenzene with a lithium base in the presence of a solvent to form (5-bromo-2-fluorophenyl)lithium, reacting (5-bromo-2-fluorophenyl)lithium with a tri($C_1$–$C_6$alkyl) borate to form a di($C_1$–$C_6$alkyl) 5-bromo-2-fluorobenzeneboronate, hydrolyzing the di($C_1$–$C_6$alkyl) 5-bromo-2-fluorobenzeneboronate to form 5-bromo-2-fluorobenzeneboronic acid, oxidizing 5-bromo-2-fluorobenzeneboronic acid to form 5-bromo-2-fluorophenol, reacting 5-bromo-2-fluorophenol with bromobenzene and a base such as a sodium hydride to form 5-bromo-2-fluorophenyl ether, reacting 5-bromo-2-fluorophenyl phenyl ether with magnesium to form a magnesium bromide of formula II, and reacting the formula II compound with an alkene compound of formula III in the presence of a transition metal catalyst such as cuprous halide, cuprous cyanide or $Li_2CuCl_4$ to form the desired fluoroolefin of formula I. The fluoroolefin compound is useful in a pesticide composition.

The reaction scheme for the preparation of the fluoroolefin compound is shown in Flow Diagram II.

Flow Diagram II

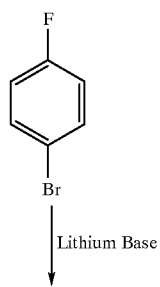

7
-continued

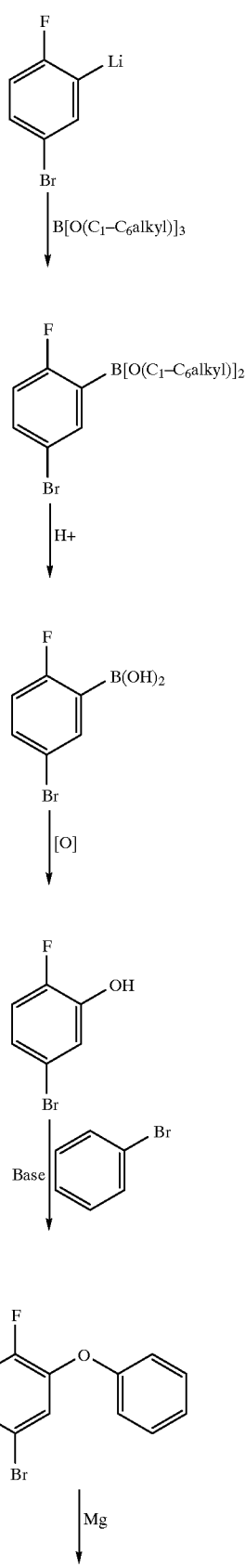

8
-continued

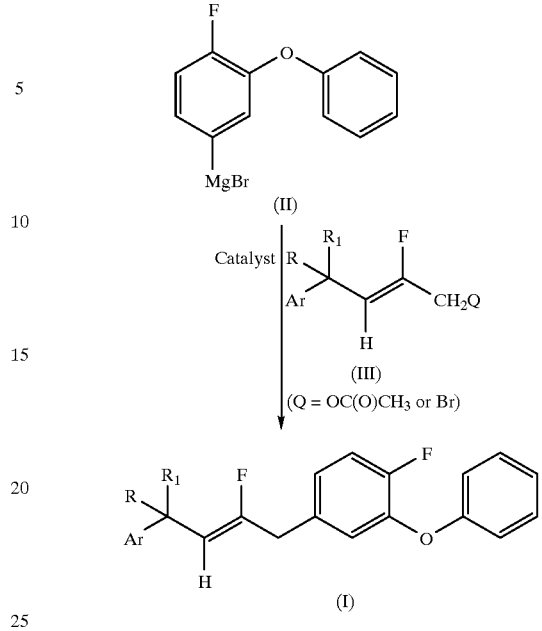

I claim:

1. A process for the preparation of 5-bromo-2-fluorobenzeneboronic acid which comprises lithiating 1-bromo-4-fluorobenzene with at least about one molar equivalent of a lithium base in the presence of a solvent to form (5-bromo-2-fluorophenyl)lithium, reacting (5-bromo-2-fluorophenyl)lithium with a tri($C_1$–$C_6$alkyl) borate to form a di($C_1$–$C_6$alkyl) 5-bromo-2-fluorobenzeneboronate, and hydrolyzing the di($C_1$–$C_6$alkyl) 5-bromo-2-fluorobenzeneboronate.

2. The process according to claim 1 wherein 1-bromo-4-fluorobenzene is lithiated with the lithium base at a temperature below about 0° C.

3. The process according to claim 2 wherein the temperature is below about –40° C.

4. The process according to claim 1 wherein the lithium base is a lithium dialkylamide or a lithium cyclic amide.

5. The process according to claim 4 wherein the lithium base is lithium diisopropyl amide.

6. The process according to claim 1 wherein the solvent is an ether.

7. The process according to claim 6 wherein the ether is tetrahydrofuran.

8. The process according to claim 1 wherein the tri ($C_1$–$C_6$alkyl) borate is trimethyl borate.

9. The process according to claim 1 wherein the di($C_1$–$C_6$alkyl) 5-bromo-2-fluorobenzeneboronate is hydrolyzed with an aqueous organic acid or an aqueous mineral acid.

10. A process for the preparation of 5-bromo-2-fluorobenzeneboronic acid which comprises lithiating 1-bromo-4-fluorobenzene with at least about one molar equivalent of a lithium base selected from the group consisting of a lithium dialkylamide and a lithium cyclic amide in the presence of an ether to form (5-bromo-2-fluorophenyl)lithium, reacting (5-bromo-2-fluorophenyl) lithium with a tri($C_1$–$C_6$alkyl) borate to form a di($C_1$–$C_6$alkyl) 5-bromo-2-fluorobenzeneboronate, and hydrolyzing the di($C_1$–$C_6$alkyl) 5-bromo-2-fluorobenzeneboronate with an aqueous organic acid or an aqueous mineral acid.

* * * * *